United States Patent
Horng et al.

(10) Patent No.: US 10,506,981 B2
(45) Date of Patent: Dec. 17, 2019

(54) VITAL SIGN DETECTION SYSTEM WITH RANDOM BODY MOVEMENT CANCELLATION

(71) Applicant: NATIONAL SUN YAT-SEN UNIVERSITY, Kaohsiung (TW)

(72) Inventors: Tzyy-Sheng Horng, Kaohsiung (TW); Fu-Kang Wang, Kaohsiung (TW); Mu-Cyun Tang, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 300 days.

(21) Appl. No.: 15/807,707

(22) Filed: Nov. 9, 2017

(65) Prior Publication Data
US 2018/0338730 A1    Nov. 29, 2018

(30) Foreign Application Priority Data
May 26, 2017    (TW) .............................. 106117757 A (51) Int. Cl.
*A61B 5/00*    (2006.01)
*A61B 5/05*    (2006.01)
(Continued)

(52) U.S. Cl.
CPC .......... *A61B 5/7207* (2013.01); *A61B 5/0507* (2013.01); *A61B 5/1135* (2013.01);
(Continued)

(58) Field of Classification Search
CPC . A63B 2200/89; A61B 5/7207; A61B 5/0507; A61B 5/1135; A61B 5/00;
(Continued)

(56) References Cited

U.S. PATENT DOCUMENTS 3,951,134 A * 4/1976 Malech ............... A61B 5/0006
                                                        600/544
4,991,585 A * 2/1991 Mawhinney ......... A61B 5/0507
                                                        340/573.1
(Continued)

FOREIGN PATENT DOCUMENTS

CN    101394783 B    3/2014
CN    102608435 B    4/2016
(Continued)

OTHER PUBLICATIONS

Mu-Cyan Tang et al., "Vital-sign detection based on a passive WiFi radar", Sep. 21-23, 2015, 2015 IEEE MTT-S 2015 International Microwave Workshop Series on RF and Wireless Technologies for Biomedical and Healthcare Applications (IMWS-BIO), pp. 74-75.*
(Continued)

*Primary Examiner* — Pascal M Bui Pho
*Assistant Examiner* — Adil Partap S Virk
(74) *Attorney, Agent, or Firm* — Jackson IPG PLLC; Demian K. Jackson (57) ABSTRACT

A vital sign detection system includes a radar device, a nonreciprocal network, a first antenna and a second antenna. An output signal from the radar device is delivered to the first antenna via the nonreciprocal network and then transmitted to a first side of a biological subject via the first antenna. A first reflection signal from the first side of the biological subject is received by the first antenna and then delivered to the second antenna via the nonreciprocal network and then transmitted to a second side of the biological subject via the second antenna. A second reflection signal from the second side of the biological subject is received by the second antenna and then delivered to the radar device via the nonreciprocal network for vital sign detection with random body movement cancellation.

12 Claims, 5 Drawing Sheets

(51) Int. Cl.
*G01S 13/58* (2006.01)
*G01S 13/00* (2006.01)
*G01S 7/35* (2006.01)
*A61B 5/113* (2006.01)
*G01S 13/88* (2006.01)

(52) U.S. Cl.
CPC ............ *G01S 7/354* (2013.01); *G01S 13/003* (2013.01); *G01S 13/583* (2013.01); *G01S 13/88* (2013.01)

(58) Field of Classification Search
CPC ...... G01S 7/354; G01S 13/003; G01S 13/583; G01S 13/88
See application file for complete search history.

(56) References Cited

U.S. PATENT DOCUMENTS

| | | | | |
|---|---|---|---|---|
| 7,272,431 | B2 * | 9/2007 | McGrath | A61B 5/024 600/509 |
| 8,259,002 | B2 * | 9/2012 | Vacanti | G01S 7/4008 342/120 |
| 8,721,554 | B2 * | 5/2014 | Lin | A61B 5/05 600/484 |
| 8,754,772 | B2 | 6/2014 | Horng et al. | |
| 2005/0143667 | A1 * | 6/2005 | Park | A61B 5/0002 600/509 |
| 2008/0074307 | A1 * | 3/2008 | Boric-Lubecke | A61B 5/0205 342/28 |
| 2008/0146944 | A1 * | 6/2008 | Tao | A61B 5/0205 600/481 |
| 2013/0245437 | A1 * | 9/2013 | Gamble | A61B 5/746 600/430 |
| 2014/0123763 | A1 * | 5/2014 | Horng | A61B 5/113 73/657 |
| 2015/0378017 | A1 * | 12/2015 | Ferguson | G01S 13/882 342/120 |
| 2016/0154098 | A1 * | 6/2016 | Pu | G01S 13/04 342/27 |
| 2016/0336989 | A1 * | 11/2016 | Lin | H04L 27/0002 |

FOREIGN PATENT DOCUMENTS

CN 105816183 A 8/2016
TW I515447 1/2016

OTHER PUBLICATIONS

Mu-Cyun Tang et al., A Single Radar-Based Vital Sign Monitoring System with Resistance to Large Body Motion, International Microwave Symposium 2017, Jun. 7, 2017.
Taiwanese Notice of Allowance dated Oct. 23, 2017 for Taiwanese Patent Application No. 106117757, 3 pages.

* cited by examiner

VITAL SIGN DETECTION SYSTEM WITH RANDOM BODY MOVEMENT CANCELLATION

FIELD OF THE INVENTION

This invention generally relates to a vital sign detection system, and more particularly to a vital sign detection system able to eliminate the random body movement effect of a biological subject.

BACKGROUND OF THE INVENTION

Doppler radar has been utilized to monitor the vital signs of a biological subject (e.g. respiration and heartbeat) for many years because of the advantage of non-contact. The Doppler radar transmits a wireless signal to the biological subject and then receives a reflection signal from the biological subject, wherein the reflection signal contains the Doppler phase shifts due to the vital signs of the biological subject, and the vital signs of the biological subject can be extracted by analyzing the reflection signal. However, the random body movements of the biological subject also cause the Doppler phase shifts in the reflection signal, making the extraction of the vital signs of the biological subject difficult because any slight movements of the body produce large-magnitude Doppler phase shifts that overwhelm those associated with the vital signs. The application of the Doppler radar to vital sign detection is therefore limited, and the elimination of the Doppler phase shifts resulting from the random body movements has become important recently for the Doppler radar vital sign detection system.

Please refer to the patents U.S. Pat. Nos. 8,721,554 and 8,754,772 for the prior art that uses two radar devices on the opposite sides of a human subject in a vital sign detection system. The subject's tiny movements due to vital signs relative to the two radar devices are in the same direction and thus the resultant Doppler phase shifts detected by the two radar devices are in phase. In contrast, the subject's body movements relative to the two radar devices are in opposite directions, and therefore the resultant Doppler phase shifts detected by the two radar devices are out of phase. According to the above characteristic, the Doppler phase shifts due to body movements can be cancelled out in the baseband (U.S. Pat. No. 8,721,554) or the RF front-end (U.S. Pat. No. 8,754,772) of the system, while the Doppler phase shifts due to vital signs can be preserved. However, the use of two radar devices increases the complexity of the system and its power consumption. Moreover, the system can tolerate only small body movements because large body movements commonly generate the nonlinear distortions and so cause great difficulty in extracting the vital signs. In a word, the prior art is difficult to monitor the vital signs of people who make large body movements.

SUMMARY

The primary object of the present invention is to provide a Doppler radar vital sign detection system with a nonreciprocal network that can transmit a signal to and receive a reflected signal from one side of a biological subject, and then retransmit the just-received signal to and receive a final reflected signal from the other side of the biological subject. When the biological subject moves randomly, the Doppler phase shifts due to body movements in the final reflected signal will be cancelled, while the Doppler phase shifts due to vital signs will be preserved. Hence, the present invention can use a single radar device to detect the vital signs of the biological subject who can make large body movements.

The vital sign detection system of the present invention includes a radar device, a nonreciprocal network, a first antenna and a second antenna. The radar device is configured to output an output signal. The nonreciprocal network is coupled to the radar device, the first antenna and the second antenna. The output signal from the radar device is configured to be delivered to the first antenna via the nonreciprocal network and then transmitted to a first side of a biological subject via the first antenna. A first reflection signal from the first side of the biological subject is received by the first antenna and configured to be delivered to the second antenna via the nonreciprocal network and then transmitted to a second side of the biological subject via the second antenna. A second reflection signal from the second side of the biological subject is received by the second antenna and configured to be delivered to the radar device via the nonreciprocal network for vital sign detection with random body movement cancellation.

A radar signal can be transmitted and retransmitted to two sides of the biological subject via two antennas with the help of the nonreciprocal network, resulting in the cancellation of the Doppler phase shifts caused by the body movements. Therefore, the present invention can use a single radar device which doesn't require high dynamic range to monitor the vital signs of the biological subject who moves over a large range.

DETAILED DESCRIPTION OF THE INVENTION

Figure 1:
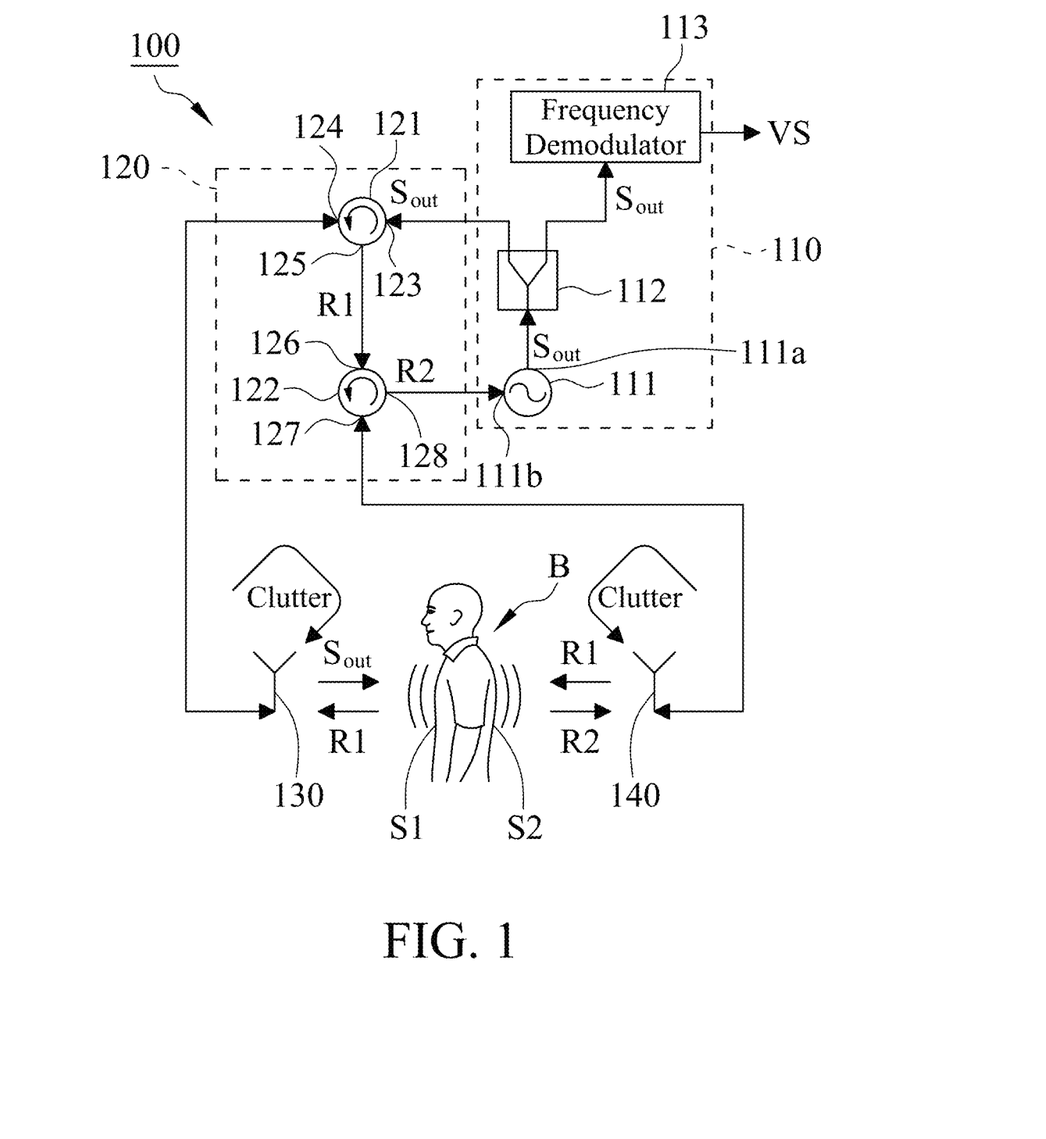
FIG. 1 is a circuit diagram illustrating a vital sign detection system in accordance with a first embodiment of the present invention.

With reference to FIG. 1, it is a circuit diagram of a vital sign detection system 100 in accordance with a first embodiment of the present invention. The vital sign detection system 100 includes a radar device 110, a nonreciprocal network 120, a first antenna 130 and a second antenna 140, wherein the nonreciprocal network 120 is coupled to the radar device 110, the first antenna 130 and the second antenna 140.

With reference to FIG. 1, the radar device 110 is configured to output an output signal $S_{out}$, wherein the radar device 110 may be a pulsed radar, a continuous-wave radar or a self-injection-locked radar. In this embodiment, the radar device 110 is a self-injection-locked radar. The radar device 110 includes an injection-locked oscillator (ILO) 111, a power splitter 112 and a frequency demodulator 113. The ILO 111 includes an output port 111a and an injection port 111b, wherein the output port 111a is configured to output the output signal $S_{out}$, and the output frequency of the ILO 111 is controlled by a voltage signal (not shown). The power splitter 112 is coupled to the ILO 111 and configured to split the output signal $S_{out}$ into two paths, wherein the output signal $S_{out}$ of one path is delivered to the nonreciprocal network 120, and the output signal $S_{out}$ of the other path is delivered to the frequency demodulator 113 for frequency demodulation to obtain a vital sign signal VS.

Figure 2:
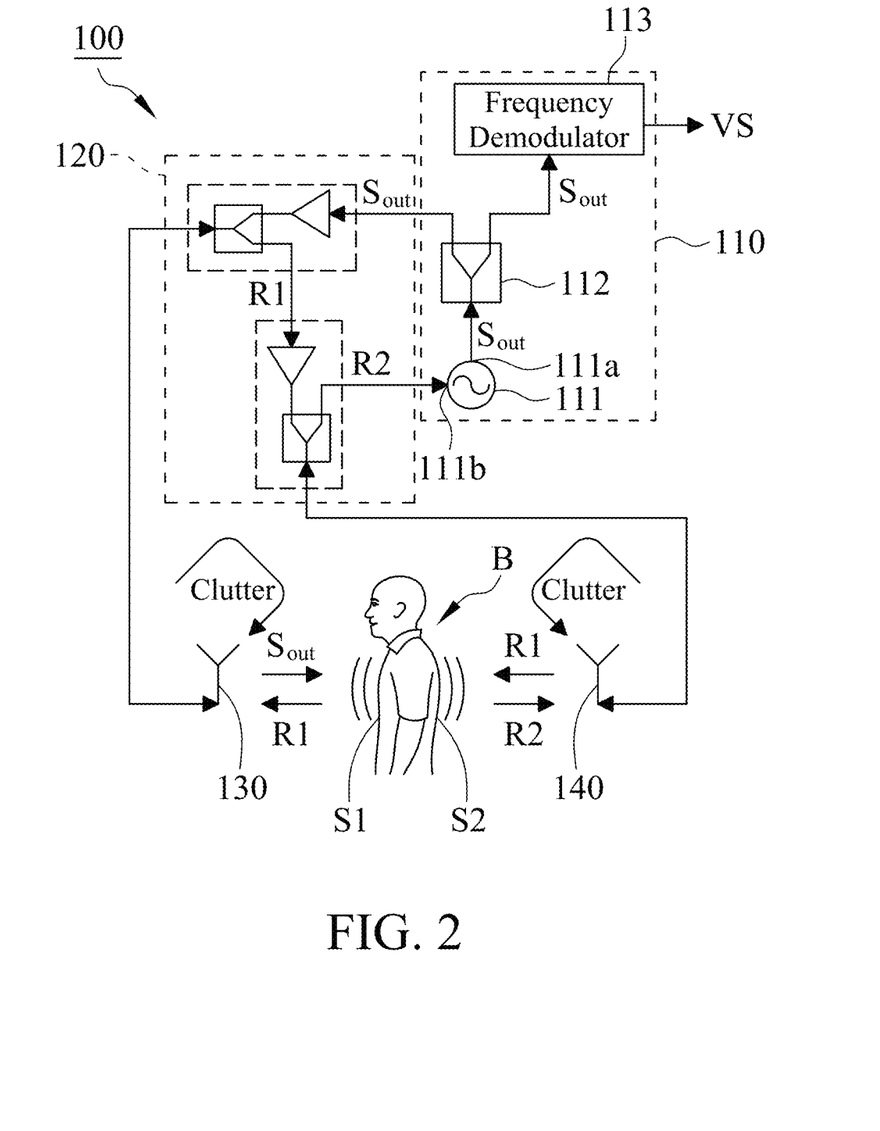
FIG. 2 is a circuit diagram illustrating the vital sign detection system in accordance with the first embodiment of the present invention.

With reference to FIGS. 1 and 2, the nonreciprocal network 120 may use ferrite components like circulators, active circuits like combined amplifiers and splitters or integrated circuits. In this embodiment, the nonreciprocal network 120 uses a first circulator 121 and a second circulator 122.

With reference to FIG. 1, the first circulator 121 includes a first port 123, a second port 124 and a third port 125, wherein the first port 123 of the first circulator 121 is electrically connected to the power splitter 112 of the radar device 110 for receiving the output signal $S_{out}$, the second port 124 of the first circulator 121 is electrically connected to the first antenna 130, and the third port 125 of the first circulator 121 is electrically connected to the second circulator 122. Moreover, the signal delivered to the first port 123 is only output from the second port 124, the signal delivered to the second port 124 is only output from the third port 125, and the signal delivered to the third port 125 is only output from the first port 123. Consequently, the output signal $S_{out}$ from the radar device 110 is input to the first port 123 of the first circulator 121, and then delivered to the first antenna 130 via the second port 124 of the first circulator 121.

The first antenna 130 is configured to transmit the output signal $S_{out}$ to a first side S1 of a biological subject B, and a first reflection signal R1 from the biological subject B is received by the first antenna 130. The first reflection signal R1 is then delivered to the second port 124 of the first circulator 121 and then delivered to the second circulator 122 via the third port 125 of the first circulator 121. Moreover, the first reflection signal R1 contains the Doppler phase shifts caused by the body and vital sign movements on the first side S1 of the biological subject B.

With reference to FIG. 1, the second circulator 122 includes a fourth port 126, a fifth port 127 and a sixth port 128. The fourth port 126 of the second circulator 122 is electrically connected to the third port 125 of the first circulator 121, the fifth port 127 of the second circulator 122 is electrically connected to the second antenna 140, and the sixth port 128 of the second circulator 122 is electrically connected to the ILO 111 of the radar device 110, wherein the signal delivered to the fourth port 126 is only output from the fifth port 127, the signal delivered to the fifth port 127 is only output from the sixth port 128, and the signal delivered to the sixth port 128 is only output from the fourth port 126. For this reason, the first reflection signal R1 output from the third port 125 of the first circulator 121 is delivered to the fourth port 126 of the second circulator 122, and then delivered to the second antenna 140 via the fifth port 127 of the second circulator 122.

The second antenna 140 is configured to transmit the first reflection signal R1 to a second side S2 of the biological subject B. A second reflection signal R2 from the second side S2 of the biological subject B is received by the second antenna 140. The second reflection signal R2 is then delivered to the fifth port 127 of the second circulator 122, and then delivered to the ILO 111 of the radar device 110 via the sixth port 128 of the second circulator 122. Moreover, the second reflection signal R2 contains the Doppler phase shifts caused by the body and vital sign movements on the first and second sides S1, S2 of the biological subject B.

With reference to FIG. 1, the first and second sides S1, S2 are the opposite sides of the biological subject B in this embodiment, therefore the biological subject B moves toward one of the antennas and simultaneously far away from the other antenna. For this reason, the random body movements of the biological subject B cause two out-of-phase Doppler phase shifts in the second reflection signal R2. On the contrary, the vital sign movements of the biological subject B (e.g. chest expansion and contraction due to cardiopulmonary activity) relative to the first and second antennas 130, 140 are in the same direction, resulting in two in-phase Doppler phase shifts in the second reflection signal R2. Therefore, the Doppler phase shifts due to body movements in the second reflection signal R2 will be cancelled out, while those due to vital signs in the second reflection signal R2 will be preserved.

With reference to FIG. 1, the second reflection signal R2 output from the sixth port 128 of the second circulator 122 is delivered to the injection port 111b of the ILO 111 to make the ILO 111 operate in a self-injection-locked state. In this state, the Doppler phase shifts in the second reflection signal R2 frequency-modulate the output signal $S_{out}$ from the ILO 111, hence the frequency demodulator 113 receives and demodulates the output signal $S_{out}$ from the power splitter 112 to obtain the vital sign signal VS of the biological subject B.

With the help of the nonreciprocal network 120, the first antenna 130 and the second antenna 140, the vital sign detection system 100 of the present invention transmits and retransmits a radar signal to the first and second sides S1, S2 of the biological subject B, and then receives the radar signal to detect the vital sign signal VS of the biological subject B. When the biological subject B moves randomly, the Doppler phase shifts due to body movements in the received radar signal will be cancelled, while the Doppler phase shifts due to vital signs will be preserved. For this reason, only one radar device 110 which doesn't require high dynamic range is used in the vital sign detection system 100 of the present invention, and only one ILO 111 is used in the single radar device 110. Moreover, the vital sign detection system 100 of the present invention can tolerate the large body movements of the biological subject B who is monitored in a line-of-sight position between the first and second antennas 130, 140.

Figure 3:
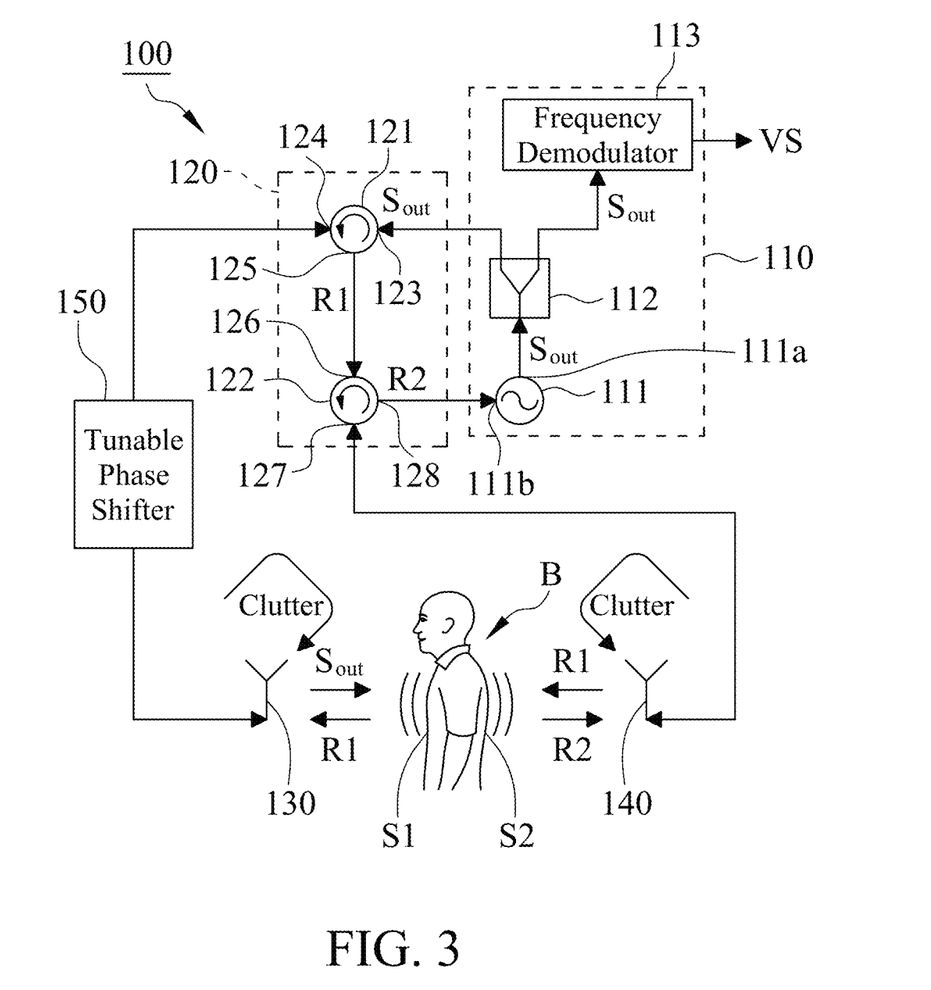
FIG. 3 is a circuit diagram illustrating a vital sign detection system in accordance with a second embodiment of the present invention.

With reference to FIG. 1, while the first and second antennas 130, 140 respectively receive the first and second reflection signals R1, R2 from the first and second sides S1, S2 of the biological subject B, they also receive the clutter from the environment, which may affect the cancellation of body movements. With reference to FIG. 3, the vital sign detection system 100 of a second embodiment preferably further includes a tunable phase shifter 150 which is coupled with the nonreciprocal network 120 and the first antenna 130. In this embodiment, one end of the tunable phase shifter 150 is electrically connected to the second port 124 of the first circulator 121, and the other end of the tunable phase shifter 150 is electrically connected to the first antenna 130. The tunable phase shifter 150 is configured to adjust the phase of the signals passing through the path between the nonreciprocal network 120 and the first antenna 130 to reduce the clutter effect on the random body movement cancellation, so the vital signs of the biological subject B can be detected accurately.

Figure 4:
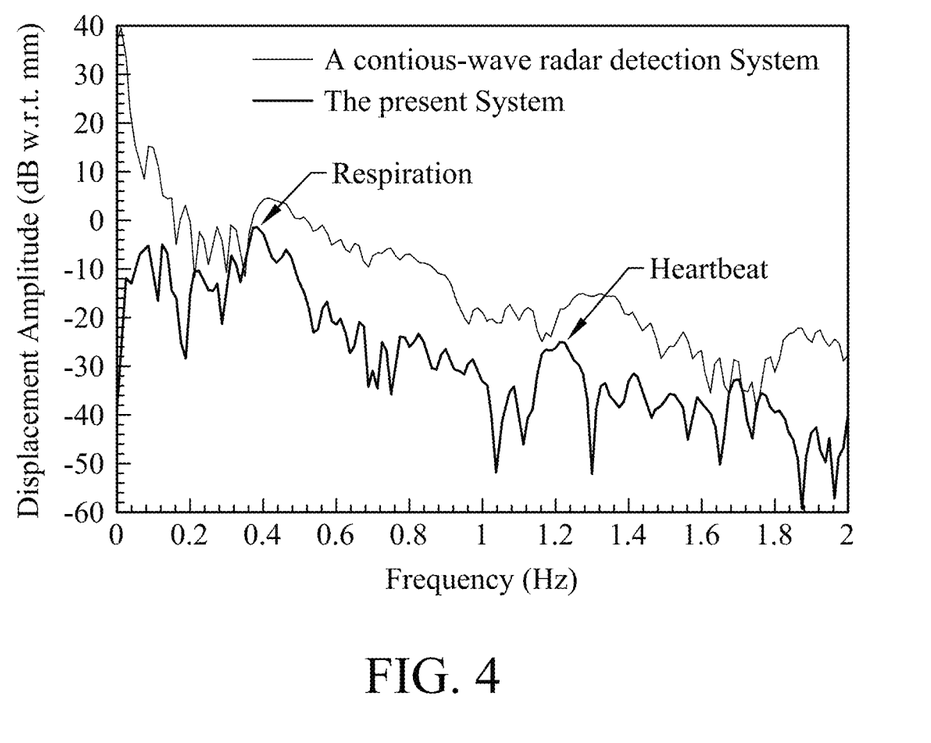
FIG. 4 is a comparison of the amplitude of the spectral components of the movement waveforms obtained by the vital sign detection system in accordance with the second embodiment of the present invention and a continuous-wave radar detection system without the nonreciprocal network.

With reference to FIG. 4, it compares the amplitude of the spectral components of the movement waveforms obtained by using the vital sign detection system 100 of the second embodiment and a continuous-wave radar detection system without the nonreciprocal network 120 to monitor a human subject who makes large body movements. In FIG. 4, the vital signs of respiration and heartbeat cannot be identified in the results coming from the continuous-wave radar detection system because of the body movements effect, but can be clearly seen in the results coming from the vital sign detection system 100 of the present invention.

Figure 5:
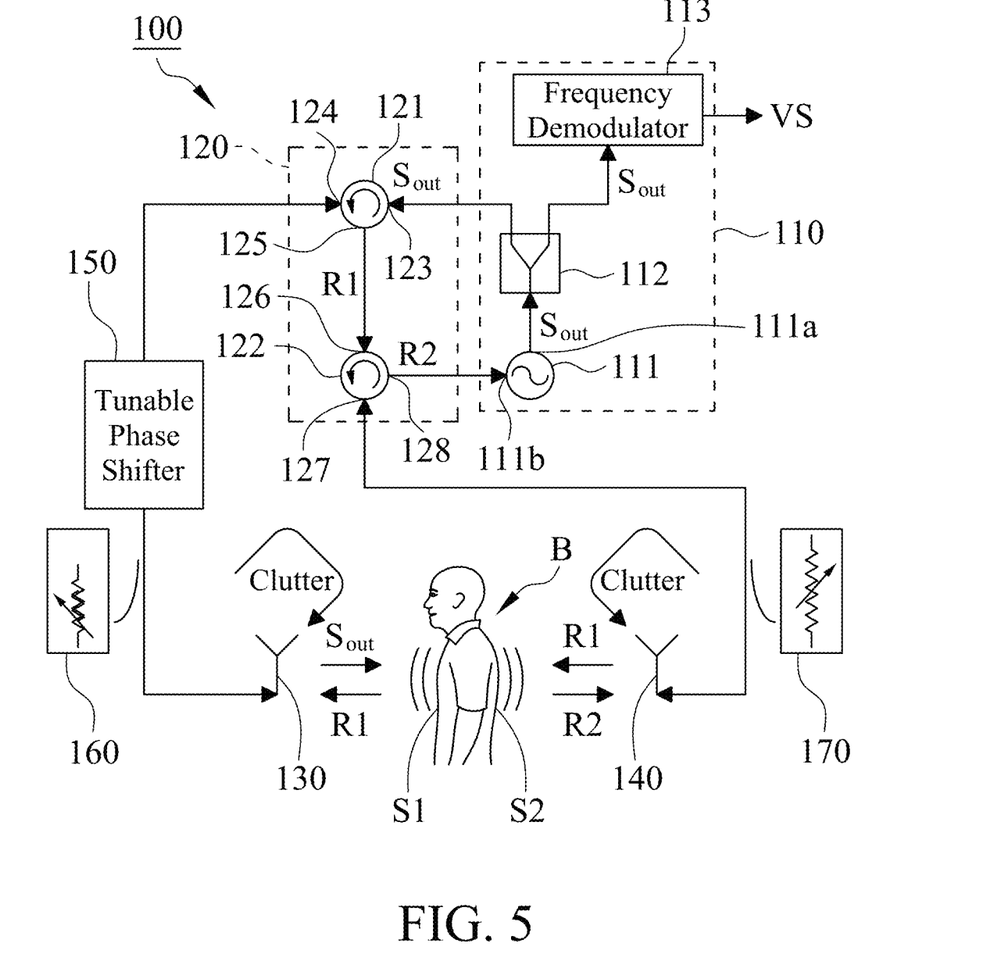
FIG. 5 is a circuit diagram illustrating a vital sign detection system in accordance with a third embodiment of the present invention.

A vital sign detection system 100 of a third embodiment is illustrated in FIG. 5. The difference of the third embodiment from the second embodiment is that the vital sign detection system 100 further includes a first clutter adjustment circuit 160 and a second clutter adjustment circuit 170, wherein the first clutter adjustment circuit 160 is configured to adjust the amplitude of the clutter received by the first antenna 130, and the second clutter adjustment circuit 170 is configured to adjust the amplitude of the clutter received by the second antenna 140, wherein the first clutter adjustment circuit 160 and the second clutter adjustment circuit 170 can be a combined coupler and variable attenuator. Thanks to the inclusion of the first and second clutter adjustment circuits 160, 170 in the vital sign detection system 100, the reduction of the clutter effect on the random body movement cancellation by using the tunable phase shifter 150 can be further improved even though the biological subject B is located at various line-of-sight positions between the first and second antennas 130, 140.

The present invention utilizes the nonreciprocal network 120 to transmit and retransmit a radar signal to two sides of the biological subject B such that the Doppler phase shifts due to body movements are cancelled but those due to vital signs are preserved and can be detected by the radar device 110. Accordingly, the vital sign detection system 100 of the present invention can tolerate the large body movements of the biological subject B to accurately perform vital sign monitoring by using the single radar device 110 which doesn't require high dynamic range.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A vital sign detection system comprising:
a radar device configured to output an output signal;
a nonreciprocal network coupled to the radar device;
a first antenna coupled to the nonreciprocal network; and
a second antenna coupled to the nonreciprocal network;
wherein the output signal from the radar device is configured to be delivered to the first antenna via the nonreciprocal network and then transmitted to a first side of a biological subject via the first antenna, and a first reflection signal from the first side of the biological subject is received by the first antenna and configured to be delivered to the second antenna via the nonreciprocal network and then transmitted to a second side of the biological subject via the second antenna, and a second reflection signal from the second side of the biological subject is received by the second antenna and configured to be delivered to the radar device via the nonreciprocal network.

2. The vital sign detection system in accordance with claim 1, wherein the radar device includes an injection-locked oscillator (ILO), a power splitter and a frequency demodulator, the ILO includes an output port configured to output the output signal and an injection port configured to receive the second reflection signal for operation in a self-injection-locked state, the power splitter is coupled to the ILO and configured to divide the output signal into two paths, the output signal of one path is configured to be delivered to the nonreciprocal network, and the output signal of the other path is configured to be delivered to the frequency demodulator for outputting a vital sign signal.

3. The vital sign detection system in accordance with claim 1, wherein the nonreciprocal network is configured to deliver the output signal from the radar device to the first antenna for transmission, and then deliver the first reflection signal received by the first antenna to the second antenna for retransmission, and then deliver the second reflection signal received by the second antenna to the radar device for vital sign detection with random body movement cancellation.

4. The vital sign detection system in accordance with claim 1, wherein the first and second sides are the opposite sides of the biological subject.

5. The vital sign detection system in accordance with claim 1, wherein only one radar device is used in the vital sign detection system.

6. The vital sign detection system in accordance with claim 2, wherein only one ILO is used in the radar device.

7. The vital sign detection system in accordance with claim 3, wherein the nonreciprocal network is composed of a first circulator and a second circulator.

8. The vital sign detection system in accordance with claim 7, wherein the first circulator includes a first port, a second port and a third port, and the second circulator includes a fourth port, a fifth port and a sixth port, and wherein the first port of the first circulator is electrically connected to the radar device, the second port of the first circulator is electrically connected to the first antenna, the third port of the first circulator is electrically connected to the fourth port of the second circulator, the fifth port of the second circulator is electrically connected to the second antenna, and the sixth port of the second circulator is electrically connected to the radar device.

9. The vital sign detection system in accordance with claim 1 further comprises a tunable phase shifter, wherein the tunable phase shifter is coupled to the nonreciprocal network and the first antenna and configured to adjust the phase of the signals passing through the path between the nonreciprocal network and the first antenna.

10. The vital sign detection system in accordance with claim 9, wherein the nonreciprocal network is composed of a first circulator and a second circulator.

11. The vital sign detection system in accordance with claim 10, wherein the first circulator includes a first port, a second port and a third port, and the second circulator includes a fourth port, a fifth port and a sixth port, and wherein the first port of the first circulator is electrically connected to the radar device, the second port of the first circulator is electrically connected to the tunable phase shifter, the third port of the first circulator is electrically connected to the fourth port of the second circulator, the fifth port of the second circulator is electrically connected to the second antenna, and the sixth port of the second circulator is electrically connected to the radar device.

12. The vital sign detection system in accordance with claim 11 further comprises a first clutter adjustment circuit and a second clutter adjustment circuit, wherein the first clutter adjustment circuit is configured to adjust an amplitude of a clutter received by the first antenna and the second clutter adjustment circuit is configured to adjust an amplitude of a clutter received by the second antenna.

* * * * *